United States Patent [19]

Gardella, Jr. et al.

[11] Patent Number: 5,266,309
[45] Date of Patent: Nov. 30, 1993

[54] REFUNCTIONALIZED OXYFLUOROPOLYMERS

[75] Inventors: Joseph A. Gardella, Jr.; Terrence G. Vargo, both of Buffalo, N.Y.

[73] Assignee: The Research Foundation of State University of New York, Albany, N.Y.

[21] Appl. No.: 522,532

[22] Filed: May 11, 1990

Related U.S. Application Data

[63] Continuation-in-part of Ser. No. 328,852, Mar. 27, 1989, Pat. No. 4,946,903.

[51] Int. Cl.⁵ ...................... A61K 31/74; A61K 31/80
[52] U.S. Cl. ............... 424/78.09; 525/326.4; 525/326.2; 424/78.17
[58] Field of Search .................. 525/326.4, 326.2, 673; 424/78.09

[56] References Cited

U.S. PATENT DOCUMENTS 4,051,161  9/1977  Proskow ........................ 544/216
4,946,903  8/1990  Gardella et al. ............... 525/326.4

OTHER PUBLICATIONS

Richard P. Haugland, Molecular Probes, Handbook of Fluorescent Probes and Research Chemicals, pp. 29–33 1989.
Barry Arkles, Chemtech, 1983, 13, pp. 542–555.

*Primary Examiner*—Thurman K. Page
*Assistant Examiner*—S. Gardner
*Attorney, Agent, or Firm*—Howard M. Ellis

[57] ABSTRACT

Fluoropolymers modified by radio frequency glow discharge in the presence of vapor/gas plasma provides for permanent and controlled substitution of hydrogen and oxygen functionality for fluorine. The oxygen-containing sites of the modified fluoropolymer are highly reactive, enabling the material to be readily refunctionalized by the introduction of a new atom, functionality or macromolecular unit, such as organosilane, alkali metal or reactive fluorescent compound.

17 Claims, No Drawings

REFUNCTIONALIZED OXYFLUOROPOLYMERS

CROSS REFERENCE TO RELATED APPLICATION

This application is a continuation-in-part of Ser. No. 07/328,852, filed Mar. 27, 1989, now U.S. Pat. No. 4,946,903.

BACKGROUND OF THE INVENTION

The present invention relates generally to novel fluoropolymers, and more specifically, to refunctionalized oxyfluoropolymers, methods of making and articles manufactured therefrom.

Fluorinated polymers, such as fluorohydrocarbon polymers, e.g., polyvinylidene fluoride, polyvinyl fluoride (PVF), including the well-known fluorocarbon polymers, e.g., perfluorinated materials, such as PTFE, are characterized by extreme inertness, high thermal stability, hydrophobicity, and a low coefficient of friction as to resist adhesion to almost any material. While these properties are highly desirable, it would also be advantageous to modify some of the polymers' characteristics in order to expand the scope of their useful applications. For instance, in the field of biocompatible materials fluorocarbon polymers in various forms have been developed, but because of their chemical inertness and extremely low reactivity the scope of these improved devices, such as implantable prosthetic devices and probes has been limited. In the field of membranes and filters, fluoropolymers have also had limited applications due to low surface energy problems associated with these materials. Membranes and filters fabricated from PTFE, for example, are unable to selectively inhibit permeation of liquids with high surface tensions (>50 dynes/cm) while allowing liquids having lower surface tensions to pass through. PTFE has also been under intense study for applications in cell culture growth membranes, but a principal shortcoming has been the inability of cells to adhere to this low energy material.

Effort of others to modify the properties of fluoropolymers have not been totally satisfactory. U.S. Pat. No. 4,548,867 (Ueno et al), for example, discloses a fluorine-containing synthetic resin having improved surface properties as evidenced by increased wettability with water, printability and susceptibility to adhesive bonding. The fluoropolymer is exposed to a low temperature plasma comprising an organic nitrogen-containing gas. Instead of modifying the atomic composition of the fluoropolymer starting material, Ueno et al form a thin "layer" of a nitrogen-containing wettable material thereto. Consequently, the adherence of such an overcoating tends to alter the microstructural morphology of the original polymer, especially with respect to pore size. This coating also alters desirable surface properties exhibited by the original fluorinated material.

Others have attempted the use of glow discharge and corona treatments to produce surface modifications. In some early work, Schonhorn and Hansen found that exposure of polyolefins and perfluorinated polymers to low power radio frequency electrodeless discharges in inert gas atmospheres produced favorable results over wet chemical methods. Their improvement in the bondability of surfaces was limited and attributed to the formation of a highly cross-linked surface layer. Studies of Hollahan et al, *J. Polym. Sci.*, 13, 807 (1969) aimed at rendering polymer surfaces biocompatible included the interaction of PTFE with plasmas excited in ammonia and nitrogen/hydrogen mixtures, the goal being the introduction of amino groups into the polymer surface. However, the long exposure times and high powers employed provided only limited results, and further, are thought to have produced significant changes not only in the surface chemistry, but also the native bulk properties. Morphology of the surface was also severely effected.

In another ESCA study entitled "ESCA Study of Polymer Surfaces Treated by Plasma," Yasuda et al, *J. Polym. Sci.*, Polym. Chem. Ed., 15, 991 (1977) the effects of discharges in argon and nitrogen on surface chemistry were considered on a range of polymers. PTFE was found to be particularly susceptible to defluorination and the introduction of oxygen and nitrogen moieties into the surface. Accordingly, there is need for permanently modified fluorinated polymers in which some of the original fluorine functionality is eliminated and replaced with oxygen functionality and hydrogen bonded to the carbon polymer backbone without the formation of coatings or layers while substantially preserving the original surface morphology and bulk characteristics of the unmodified material on a molecular scale.

A further manifestation of the inert characteristics of highly fluorinated polymers has been their resistance to enter directly into reactions with other substances for purposes of introducing other functionalities and developing useful new properties not normally found in fluoropolymers. It has also been discovered that when fluoropolymers are exposed to radio frequency glow discharge (RFGD) in the presence of a hydrogen gas—vapor (water, methanol or formaldehyde) mixture, a modified surface forms comprised of a controllably reduced amount of original flourine with controlled amounts of hydrogen and oxygen or oxygen-containing groups covalently bonded to the carbon backbone of the polymer. The modified oxyfluoropolymers retain the unique properties of highly fluorinated polymers, such as PTFE, with the tendency to repel water and other polar solvents, high thermal stability, low adhesion and friction coefficients. However, unlike the modifications observed by Andrade et al. (U.S. Pat. No. 4,508,606) and Ueno et al. (U.S. Pat. No. 4,548,867) it has been found that the oxyfluoropolymers have reactive chemical sites which permit bonding with other chemical functionalities, such as organo silicons to form a class of novel and useful refunctionalized fluoropolymers. Accordingly, the invention contemplates a series of novel and useful refunctionalized oxyfluoropolymers.

SUMMARY OF THE INVENTION

It is a principal object of the invention to provide for novel oxyfluoropolymers in which the atomic structure of the native fluoropolymer material is permanently modified by the elimination of some of the original fluorine functionality and the introduction of both oxygen atoms or oxygen-containing groups and hydrogen atoms covalently bonded to the original carbon polymer backbone. The morphological properties of the oxyfluoropolymers at a molecular level remain substantially unchanged from those of the starting fluoropolymer materials while wettability with respect to low surface tension liquids and surface free energy ($y_s$) as determined through critical surface tension ($y_c$) are increased. The fluoropolymer starting material used in preparation of the oxyfluoropolymers is intended to include fluorocarbon type polymers and fluorohydrocarbon polymers.

More specifically, it is an object of the invention to provide for novel oxyfluoropolymers having increased surface energies in which a portion of the surface fluorine atoms to depths of about 10 to about 100 Å of a fluoropolymer starting material are permanently substituted with hydrogen atoms, and from about 5 to about 20% of the fluorine atoms are also substituted with oxygen functionality. That is, instead of introducing a modified polymer coating to the original material, the object is to provide for oxyfluoropolymers in which the original starting material is permanently modified at the molecular level by removal of some of the fluorine so the carbon backbone has fluorine, oxygen and hydrogen atoms covalently bonded thereto. In essence, the fluoropolymer starting material has a sufficient number of fluorine atoms permanently substituted with both hydrogen atoms and oxygen functionality covalently bonded to the carbon backbone to a surface depth of about 10 to about 100 Å to increase the surface free energy ($y_s$) as determined through critical surface tension ($y_c$) while the hydrophobic, non-fouling properties are maintained.

It is a further object of the invention to provide for oxyfluoropolymers in which up to 98 percent, and more specifically, from about 20 to about 85 percent of the surface fluorine atoms to depths from 10 to about 100 Å are permanently substituted with hydrogen and oxygen and/or oxygen-containing groups of which from about 3 to about 30 percent of the substituted fluorine is replaced with oxygen or oxygen-containing groups and from about 70 to about 97 percent is substituted with hydrogen atoms. The morphological properties and bulk properties of the oxyfluoropolymer remain substantially unchanged over the starting fluoropolymer material.

The permanently modified fluoropolymers have increased wettability towards low surface tension liquids, as well as chemically reactive sites allowing for attachment of various chemical functionality to these normally inert surfaces, and as such have applications which make them especially adaptable for membrane applications, e.g., filtration membranes or other surface mediated processes, e.g., adhesion prevention or promotion; devices such as bioprobes coated with oxyfluoropolymers making them biocompatible while allowing specific ion permeability; expanded PTFE membranes especially in the field of cell culture growth membranes; and because of improved and controlled wettability properties (with respect to wanted biological processes) implantable prosthetic devices, such as bone replacements, heart valves, and the like. Further, due to the retention of the inert hydrophobic properties these materials can be used such that little or no adsorption or fouling occurs by unwanted biological species.

It is yet a further object of the invention to provide for methods of making permanently modified fluoropolymers having increased surface energy by the steps of:

a) providing a starting fluoropolymer material;
b) providing a gas/vapor plasma mixture comprising hydrogen and at least one member selected from the group consisting of water, methanol and formaldehyde; and
c) contacting said fluoropolymer material with said plasma mixture while exposing said fluoropolymer to at least one radio frequency glow discharge for a sufficient period to increase the surface free energy ($y_s$) by permanently substituting to a depth from about 10 to about 100 Å on the starting fluoropolymer, fluorine atoms with hydrogen atoms and from about 5 to about 20% of said fluorine atoms with oxygen functionality.

The methods impart surface wettability properties as well as chemically reactive sites to the original fluoropolymer without materially effecting the materials original hydrophobic properties. Plasma gas/vapor mixture concentrations of hydrogen, water, methanol, and formaldehyde together with wattage or power of the glow discharge and pressure (vacuum) are variables which determine the depth of surface modifications, as well as the respective atomic concentrations of carbon, fluorine, hydrogen and oxygen making up the modified portion of the final polymer.

The invention also contemplates refunctionalized oxyfluoropolymers comprising a fluoropolymer in which up to 98 percent of the surface fluorine atoms to depths from about 10 to about 100 Å have been permanently substituted with hydrogen and oxygen or oxygen-containing groups of which from about 3 to about 30 percent of the substituted fluorine has been replaced with the oxygen or oxygen-containing groups and from about 70 to about 97 percent of the substituted fluorine has been replaced with hydrogen atoms, and from about 3 to about 100 percent of the oxygen or oxygen-containing groups have a covalently bonded member selected from the group consisting of an organosilicon, alkali metal or isocyanate-containing fluorophores.

DETAILED DESCRIPTION OF THE INVENTION

Through radio frequency glow discharge the atomic structure of the top 10 to about 100 Å of a fluoropolymeric starting material can be permanently modified by substitution of a portion of the original fluorine functionality with oxygen or oxygen-containing groups and hydrogen covalently bonded directly to the carbon polymer backbone. By regulating amounts and ratios of carbon, fluorine, oxygen and hydrogen in the modified polymer, surface energy can be increased from that of the original material along with wettability towards non-polar aliphatic liquids properties without materially altering the corresponding hydrophobic properties, or altering the polymers original surface morphology and bulk characteristics.

In preparing the oxyfluoropolymers, useful fluoropolymer starting materials include both fluorocarbon polymers and fluorohydrocarbon polymers. This would include fluoropolymers having a carbon backbone with atoms bonded thereto consisting of either fluorine or both fluorine and hydrogen provided that when hydrogen atoms are present fluorine shall also be present in a ratio of at least 1:3. Preferably, the fluoropolymers include materials having a critical surface tension ($y_c$) ranging generally from about 15 to about 30 dynes/cm. Specific representative examples of useful low surface energy fluorocarbon polymers are the perfluorinated polymers polytetrafluoroethylene (PTFE), polymers of hexafluoropropylene and tetrafluoroethylene like fluorinated ethylene-propylene (FEP) copolymers, etc. Suitable low surface area fluorohydrocarbon starting polymers include resins like polytrifluoroethylene, poly(vinylidene fluoride) (PVDF), poly(vinyl fluoride), poly(vinyl difluoride) including piezo and pyroelectric poled PVDF and the like.

The oxyfluoropolymer compositions are especially unique in that a controllable amount from about 1 to about 98% of the fluorine atoms of the starting polymer's surface interface are permanently removed and replaced with hydrogen atoms and with oxygen atoms or low molecular weight oxygen-containing functionalities, so that all substituents are covalently bonded directly to the carbon backbone polymer chain to a depth of about 100 Å. Oxygen functionality may take the form of oxo, hydroxyl, alkoxy, like methoxy, ethoxy and propoxy or R'—CO— or combinations thereof where R' is hydrogen or alkyl, and particularly C1–C5 lower alkyl, including methyl, ethyl, propyl, isopropyl, and so on. Accordingly, unlike the nitrogen-containing monolayers/surface overcoatings of U.S. Pat. No. 4,548,867 the intrinsic atomic composition of the above starting material is permanently modified to regulated surface depths ranging from about 10 to about 100 Å, providing a novel combination of properties, i.e., chemically reactive sites, greater surface wettability and free energy enhancement of fluorinated carbons and hydrocarbons while still substantially preserving the hydrophobic properties and microstructural morphology, e.g., membranous structure, pore size, surface roughness on a molecular scale, etc.

The oxyfluoropolymers produce a wide variety of surface free energy increases where, for example, a fluoropolymer like PTFE with a $y_c$ of about 18 dynes/cm at 20° C. can be increased to about 40 dynes/cm to a depth of between 10 to 100 Å for increased wettability and other surface properties relating to the surface free energy of a material. Even with such increases in surface free energy the hydrophobic properties of the original material remain substantially intact. That is, the modified polymers of the invention having hydrogen, oxygen and fluorine functionalities are covalently bonded to the carbon polymer backbone will still inhibit surface fouling, permeation and wetting by liquids with high surface tensions, i.e., >50 dynes/cm like water and other similar polar solvents, but also being wettable by liquids having low surface tensions, i.e., <50 dynes/cm, such as blood plasma and other nonpolar organic solvents. This is quite unexpected because when the surface free energy of a polymer is increased one normally finds with the increase in wettability an equivalent decrease in the hydrophobic properties of the material. However, quite surprisingly with the increased surface energy of the oxyfluoropolymers of the present invention wettability is increased without the normally expected decrease in hydrophobicity from that of the original starting material.

The oxyfluoropolymers are prepared by a plasma treatment process in which the previously described fluoropolymers are exposed to a single or a series of relatively low power radio frequency glow discharges (RFGD). The target fluoropolymers generally can be in the form of a sheet, premolded or coated article, such as a porous PTFE membrane or filter, e.g., Goretex ®, where, for example, increased permeability of ions would be desirable without altering pore characteristics of the native material; a bioprobe of conventional design coated with Teflon ® or a molded, implantable prosthetic device where, for instance, it would be desirable to modify its adhesive and/or surface reactivity characteristics to blood platelet attachment.

Instead of a plasma treatment with purely a gas the radio frequency glow discharge is conducted in an atmosphere of a gas/vapor mixture at pressure vacuums of under 1,000 mTorr, and more preferably, from about 50 to 200 mTorr, and power loadings of less than or equal to 100 watts.

Although not wishing to be held to any precise mode of action, the primary mechanism of the plasma treatment process of the instant invention is believed to involve the transfer of energy to the gaseous ions directly to form charged ionized gas species, i.e., ion sputtering of the polymer at the gas-solid interface. The radio frequency glow discharge plasma gas ions become excited through direct energy transfer by bombarding the gas ions with electrons. Thus, by exposing the fluoropolymer material to either a single or a series of radio frequency glow discharge gas/vapor plasmas consisting of admixtures of hydrogen gas ranging from 20% to 99% by volume, and 1 to about 80% by volume of a vapor from liquids, such as water, methanol, formaldehyde and mixtures thereof, 1 to about 98% of the surface fluorine atoms are permanently removed in a controlled/regulated manner and replaced with oxygen atoms or low molecular weight oxygen-containing functionality along with hydrogen atoms. Although hydrogen is required, in all instances, by itself it is insufficient to introduce both hydrogen and oxygen moieties to the carbon polymer backbone. A nonpolymerizable vapor/$H_2$ mixture is necessary to introduce the required hydrogen and oxygen or functionalized moieties onto the fluoropolymer without disrupting surface morphology. Further, uses of pure gas mixtures, specifically $H_2/O_2$ show only limited results. Representative radio frequency glow discharge plasmas and operating conditions are provided in Table I below:

TABLE I

| Starting Material | RFGD Mix Composition | Pressure (mTorr) | Time (Min.) | Depth (Å) | CALCULATED ATOMIC RATIOS (ESCA) | | | |
|---|---|---|---|---|---|---|---|---|
| | | | | | C/O | C/F | F/O | Stoichiometry |
| Unmodified PTFE* | — | — | — | — | ∞ | 0.45 | ∞ | $C_2F_{2\,3}$ |
| Unmodified PVDF | — | — | — | — | ∞ | 1.0 | ∞ | $C_1F_1$ |
| Modified PTFE | 2% (vol) $H_2O$/98% $H_2$ | 150 | 20 | 100 | 7.5 | 1.5 | 5.0 | $C_{15}F_{10}H_{18}O_2$ |
| Modified PTFE | 2% (vol) $H_2O$/98% $H_2$ | 200 | 10 | 100 | 8.6 | 0.91 | 9.7 | $C_{17}F_{19}H_{13}O_2$ |
| Modified PTFE | 20% (vol) Methanol vapor/80% $H_2$ | 150 | 30 | 100 | 3.0 | 1.5 | 2.0 | $C_6F_4H_6O_2$ |
| Modified PTFE | 20% (vol) methanol vapor/80% $H_2$ | 200 | 5 | 100 | 9.3 | 2.0 | 4.7 | $C_{28}F_{14}H_{39}O_3$ |
| Modified | 2% (vol) $H_2O$/98% $H_2$ | 200 | 10 | 100 | 8.0 | 16.0 | 0.48 | $C_{16}F_1H_{29}O_2$ |

TABLE I-continued

| Starting Material | RFGD Mix Composition | Pressure (mTorr) | Time (Min.) | Depth (Å) | CALCULATED ATOMIC RATIOS (ESCA) | | | |
|---|---|---|---|---|---|---|---|---|
| | | | | | C/O | C/F | F/O | Stoichiometry |
| PVDF | | | | | | | | |

*Porous Goretex membrane

Through specific and controlled addition of oxygen functionality via radio frequency glow discharge the oxyfluoropolymers disclosed herein are resistant to fouling and adsorption of substances, a property which is consistent with the unmodified fluoropolymers. However, unlike unmodified fluoropolymers, such as PTFE, it was found that the oxyfluoropolymers have the unique ability to react cleanly and rapidly with various atoms, molecules or macromolecules through the oxygen containing groups of the oxyfluoropolymer, i.e. hydroxyl, carboxylic acid, ester or aldehyde to form refunctionalized oxyfluoropolymers. This is especially advantageous because generally fluoropolymers are inert to wet and physical-chemical processes, at least to those which do not also induce substantial surface morphological damage. In addition, due to the relative inertness of oxyfluoropolymers the ability to incorporate reactive functionality onto their surfaces creates a material which is specifically and controllably reactive while also being inert to other chemical and environmental concerns, i.e. adsorption of surface contaminants.

The refunctionalized fluoropolymers are useful as coatings and films, and in fiber optics, optoelectronic and biomedical devices, such as biosensors and antibody sensors. They also have uses in general applications as non-fouling substrates which can have optically, electrically, electrochemically active sensor molecules attached. The refunctionalized oxyfluoropolymers are also useful as separators and membranes in various electrochemical devices, such as batteries.

The types of functionalities which can be utilized with the oxyfluoropolymers surfaces include all those which can be reacted with hydroxyl, carboxylic acid, ester and aldehyde groups bonded through the fluoropolymer backbone by means of reactions generally familiar among those skilled in the art. The reactivity of the surface of the oxyfluoropolymer is determined by the particular type of oxygen functionality. For instance, silanes of the silicon-containing organic or inorganic class react vigorously with hydroxyl groups forming a silanol linkage or coupled bond. However, the rate of reaction is enhanced even further due to the close proximity of the reactive oxygen functionality to the electronegative fluorine atom(s). Apparently, this provides for extremely rapid reaction rates through stabilization of the oxygen anion. The preferred refunctionalized fluoropolymers may be prepared with a wide range of organosilane coupling agents of the general formula $$Y(CH_2)_n Si{-}(X)_3 \qquad (I)$$

in which Y is a member selected from the group consisting of allyl, alkyl, haloalkyl, amino, mercapto, epoxy, glicidoxy, methacrylate, cyano and —CH$_2$CO$_2$—alkyl, and n is from 0 to about 17 and X is independently selected from hydrogen, halogen, alkyl, haloalkyl, alkylamino, alkoxy and trialkylsiloxy. The silane coupling agents are known materials which are commercially available through ordinary channels of commerce, such as Petrarch Systems, Bristol, Pa.

The process of preparing the organosilicon substituted oxyfluoropolymers can be illustrated by the following reaction:

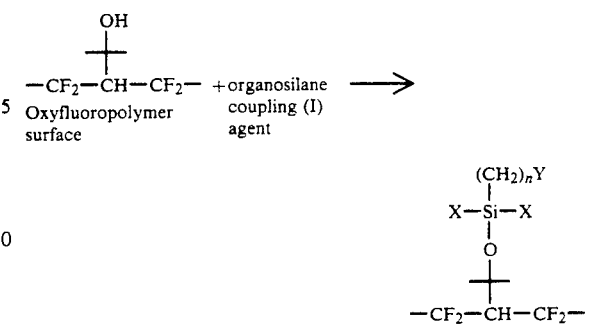

wherein the values for X, Y and n are the same as formula (I).

In addition to the organosilane coupling agents (I), the refunctionalized fluoropolymers are preferably formed from organosilane coupling agents in which Y is alkylamino, dialkylamino, mercapto or glycidoxy and in which X is chlorine, bromine, fluorine, alkyl having from 1 to 4 carbon atoms, chloromethyl, monoethylamino, dimethylamino, methoxy, ethoxy, propoxy, butoxy or trimethylsiloxy. Specific representative organosilanes are 3-aminopropyltriethoxysilane, 3-mercaptopropyltrimethoxysilane and 3-glycidoxypropyltrimethoxysilane to name but a few.

Other particularly useful functionalities which may be covalently bonded with the oxyfluoropolymers through their reactive oxygen-containing sites are the fluorophores which refers to a group of organic compounds that may fluoresce. The preferred fluorophores are the isothiocyanate substituted types, such as fluorescein isothiocyanate (FITC), malachite green isothiocyanate, rhodamines like tetramethylrhodamine isothiocyanate (TRITC), and the like, which are described in the publication by Molecular Probes, Inc., entitled Handbook of Fluorescent Probes and Research Chemicals by Richard P. Haughland, 1989, which publication is incorporated-by-reference herein. The isothiocyanate modified fluorescent compounds are also available from Molecular Probes, Inc.

The oxyfluoropolymeric substituted isothiocyanate fluorescent materials are especially useful in a wide variety of probes and sensors, such as for nucleic acids.

In addition to the organosilicon and fluorophore substituted fluoropolymers, other representative examples include alkali metal derivatives of oxyfluoropolymers:

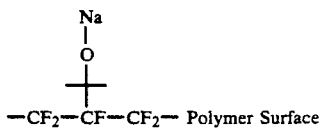

In addition to sodium oxyfluoropolymers, solutions of potassium and lithium hydroxide may be reacted with the oxygen containing groups of the oxyfluoropolymers for purposes of preparing useful alkali metal oxyfluoropolymers which can then be used in electrochemical cells, including energy producing cells, like batteries as cell separators.

The following specific examples demonstrate the various aspects of this invention, however, it is to be understood that these examples are for illustrative purposes only, and do not purport to be wholly definitive as to conditions and scope.

EXAMPLE I

Part A

To prepare oxyfluoropolymers, using radio frequency glow discharge (RFGD) a model PDC-23g RF plasma chamber having a maximum output of 100 watts from Harrick Scientific Corp., Ossining, N.Y., was modified by adding an in-line VG Model MD 95 ultra high vacuum (UHB) leak valve before the inlet side of the glow discharge unit. The UHV leak valve provided precise control of the system pressure while also allowing smooth flow of vaporized liquids into the plasma reaction chamber. In addition, a diffusion pump in conjunction with a roughing pump was installed at the outlet of the plasma reaction chamber. Optionally, a liquid nitrogen trap can be installed between the RFGD unit and the diffusion pump to protect the pump from potentially damaging vapors. Hydrogen from a flow meter, and liquids, e.g., water, methanol, formaldehyde, etc., are bled by the UH vacuum release valve to the inductively coupled plasma reaction chamber.

Through use o the diffusion pump, a base pressure of about 5 mTorr was obtainable and employed before all glow discharge treatments to effectuate a clean experimental system. By ultrasonically extracting the samples in hexanes, all trace contaminants caused by backflow of pump oil was minimized. In addition, by ultrasonically cleaning the samples, low molecular weight and evanescent surface constituents were effectively removed. This permitted more accurate analysis of permanent surface functionalities introduced into the fluoropolymer through RFGD surface modification.

Part B

A sheet of porous PTFE (Goretex) measuring 10 cm $\times$ 5 cm $\times$ 1 mm was analyzed using high resolution (17.9 eV) electron spectroscopy for chemical analysis (ESCA) to establish the true atomic percentages of carbon and fluorine present in the sample prior to glow discharge treatment. Measured peak areas of the detected atoms (carbon and fluorine) using atomic sensitivity factors gave corrected atomic percentages of 70% fluorine and 30% carbon for the sample corresponding to a $C_{1.0}F_{2.3}$ stoichiometry and a molecular structure $CF_3—(CF_2)—_n \ldots —CF_3$. Corrected binding energies of the carbon and fluorine 1s peaks indicated a totally saturated carbon backbone with no detectable oxygen.

The pure perfluorinated sheet was then placed on the sample stage in the plasma reaction chamber and exposed for 20 minutes at 100 watts to a gas/vapor RFGD plasma mixture consisting of ca. 98% by volume hydrogen and ca. 2% by volume water at 150 mTorr pressure. The sample was then subjected to ESCA analysis. The low and high resolution surveys showed C 1s, F 1s and O 1s results indicating the molecular structure. C 1s indicated the incorporation of large amounts of aliphatic C—H and —CH$_2$—CH$_2$—functionality with lesser amounts of carbon-oxygen functionality. Elemental analysis showed C 33.3%; F 22.2%; H 40.0%; O 4.5%. ATR-Infrared spectroscopic results indicated the formation of both C—O and —OH functionality.

EXAMPLE II

A second sample of the same pure porous PTFE sheet of Example I, Part B and of the same dimensions was exposed to a gas/vapor RFGD plasma mixture also consisting of 98% by volume hydrogen and 2% by volume water at 100 watts and a pressure of 200 mTorr like that of Example I, Part B. However, the exposure time was decreased from 20 to 10 minutes. The ESCA low resolution survey and high resolution C 1s, F 1s, and O 1s spectra showed the addition of oxygen and hydrogen to the molecular structure of the PTFE surface. An ATR-IR spectrum of this material also indicated incorporation of amounts of C—O and —OH functionality onto the surface portion of the sheet. Elemental analysis showed C 33.3%; F 37.3%; H 25.5%; O 3.9%.

EXAMPLE III

A sheet of shear porous PTFE (Goretex) like that used in Examples I and II was exposed to a gas/vapor RFGD plasma mixture using the laboratory set-up described above in Part A of Example I. The plasma consisted of 80% by volume hydrogen and 20% by volume methanol. Exposure time was 30 minutes at a pressure of 150 mTorr. The ESCA low resolution and high resolution C 1s, F 1s, O 1s spectra showed the introduction of oxygen at the molecular level on the PTFE surface. The C 1s ESCA spectrum indicated both aliphatic carbon and C—O functionality with a corresponding decrease in fluorinated carbon groups. The F 1s spectrum showed a large increase in peak width, indicative of two types of fluorine functional group environments residing at the PTFE surface region. The amount of oxygen functionality present in the modified oxyfluoropolymer surface was more than double that of the samples prepared in Examples I and II, as shown by the following elemental analysis: C 33.3%; F 22.0%; H 33.3%; O 11.1%. ATR-IR showed a corresponding increase in C—O and —OH functionality.

EXAMPLE IV

A sheet of polyvinylidene fluoride (PVDF) measuring 10 cm $\times$ 5 cm $\times$ 1 mm was analyzed using high resolution ESCA to establish the composition of the sample. Two peaks of almost equal area were observed which were indicative of a molecular structure containing equal amounts of CH$_2$ and CF$_2$ groups. The unmodified polymer can be described stoichiometrically as $C_{1.0}F_{1.0}H_{1.0}$ with a molecular structure of $(CH_2—CF_2)_n—$. The unmodified PVDF sheet had an elemental analysis of C 33%; F 33%; H 33%.

The sample sheet of PVDF was exposed to a gas/vapor RFGD plasma mixture for 10 minutes at a pressure of 200 mTorr at 100 watts in the laboratory set up of Example I, Part A. The gas/vapor mixture consisted of 2% by volume water and 98% by volume hydrogen. The treated sample was then analyzed using ESCA low resolution survey and high resolution C 1s, F 1s and O 1s which demonstrated an extreme drop in the fluorine signal with a corresponding increase in hydrogen and oxygen to the top surface to a depth of about 100 Å. The C 1s spectrum indicated a hydrocarbon surface with some C—O functionality and little or no C—F functionality in the top most 100 Å of the PVDF surface. ESCA analysis indicated only 2 atomic percent fluorine in the upper most 100 Å of the modified material whereas the original unmodified sheet contained 33 atomic percent fluorine. Elemental analysis of the treated PVDF was C 33.3%; F 2.1%; H 60.4%; O 4.2%.

EXAMPLE V

A sample of the same pure PTFE used in Example I, Part B, was exposed to a gas/vapor RFGD plasma mixture consisting of about 60% by volume hydrogen and 40% formaldehyde for 5 minutes at a pressure of 200 mTorr at 100 watts in the laboratory set-up of Example I, Part A. Elemental analysis by ESCA of the treated PTFE was found to be C 33.3%; F 16.7%; H 46.4%; O 3.6%. ATR-IR again indicated formation of C—O and —OH functionality.

EXAMPLE VI

Modified fluoropolymer materials (Table II below) were analyzed using a wettability profile which measures the contact angles of various liquids each having a different surface tension. This series of liquids with different surface tensions allows for the measurement of changes in wettability as related to an empirical measure of surface energy. Further, the change in hydrophilicity/hydrophobicity can also be measured through use of the higher surface tension polar liquids (i.e., water and glycerol). The critical surface tension ($y_c$) is the value given indicating the surface tension of the liquid which totally spreads on the surface in question. Liquids with surface tensions equal to or below this value will also be observed to spread, and thus, increases in $y_c$ relate an increase in surface energy allowing for greater wettability of liquids with higher surface tensions.

The contact angles of the various liquids listed in Table II were measured on each respective material employing a model 100 Rame' Hart Goniometer for measuring the angle and a freshly flamed Pt wire for placing the purified liquid drops on the material surfaces.

TABLE II

| | | Measured Contact Angles (degrees) | | | |
|---|---|---|---|---|---|
| | LIQUID/VAPOR SURFACE TENSIONS (dyne/cm) | UNMODIFIED PTFE GORTEX | MODIFIED PTFE 20 min H₂(H₂O) EXAMPLE II | UNMODIFIED PVDF | MODIFIED PVDF 10 min H₂(H₂O) EXAMPLE IV |
| Water | 72.4 | ~140° | 110° | 120° | 110° |
| Glycerol | 64.8 | 130° | 115° | 125° | 115° |
| Formamide | 58.9 | 130° | 112° | 115° | 95° |
| Thiodiglycol | 53.5 | 125° | 120° | 107° | 80° |
| Methylene Iodide | 49.0 | 120° | 115° | 102° | 25° |
| 1-Bromo-Napthalene | 45.0 | 100° | 110° | 40° | 10° |
| 1-Methyl-Napthalene | 39.3 | 100° | 90° | 10° | (spread) 0° |
| Dicyclohexyl | 32.7 | 93° | 60° | 10 | 0° |
| n-Hexadecane | 27.6 | 20° | (spread) 0° | 5° | 0° |
| n-Tridecane | 26.0 | 10° | 0° | (spread) 0° | 0° |
| n-Decane | 23.8 | (spread) 0° | 0° | 0° | 0° |

Table II shows that a decrease in contact angles as measured on the 20 minute H₂/H₂O RFGD modified Goretex was small for the liquids having surface tensions >39.3 dyne/cm indicating a retention of the original materials non-wetting characteristics for these liquids. The measured angles for these liquids also indicate the retention of surface residing fluorine functionality and especially a large degree of hydrophobicity as indicated from the angles measured for water and glycerol. Below 39.3 dyne/cm, the contact angles of the utilized liquids showed a larger degree of wettability indicating an increase in surface energy which is ascribed to the presence of small amounts of surface residing oxygen functionality earlier detected by ESCA and IR results. A 0° measurement (i.e., $y_c$) was observed at 27.6 dyne/cm for the H₂/H₂O RFGD modified Goretex as compared to 23.8 dyne/cm as measured on the unmodified Goretex membrane. This indicates an increase in surface energy again, attributed to the creation of surface residing oxygen functionality in close proximity to the fluorine functionality.

Similar observation were made on the PVDF modified material except that the surface energy showed a greater degree of enhancement (i.e., $y_c$ increased from 27.6 dyne/cm as measured on unmodified PVDF to 39.3 dyne/cm for the H₂/H₂O RFGD modified PVDF). Again, the degree of hydrophobicity showed only minor decreases as indicated by >90° (110°) measured contact angle of water on the modified PVDF surface.

These two examples illustrate only two values for $y_c$ of modified materials and measurements achieving a range of $y_c$ values (from 25-40 dyne/cm have been observed for the Goretex modified materials and 30-40 dyne/cm for the modified PVDF materials) which are dependent on RFGD conditions especially hydrogen/vapor concentration and the liquid employed as the vapor.

EXAMPLE VII

A bioprobe may be fabricated for detecting various molecules or important species in a biological system, e.g., kidney. A very low surface energy fluoropolymer, such as porous PTFE, e.g., Goretex membrane, would be a suitable starting material where total inertness is desired. However, a bio-probe would be especially desirable in this instance if ion permeability was enhanced without changing the membrane's pore structure or hydrophobic character, and at the same time the majority of the probe would remain essentially inert and nonreactive so as to prevent contamination or bio-rejection when placed in vitro. This may be accomplished by the removal of fluorine atoms and the incorporation of —OH functionality into the PTFE. Other moieties may then be introduced by reacting with these sites. Silanes, for example, may be quickly reacted with such oxygen functionalities by formation of the Si—O bond. Accordingly, through known masking techniques several modified sites may be created by exposing the polymer to gas/vapor RFGD plasma mixtures as disclosed above. Furthermore, using known masking techniques each of the modified sites may be reacted with a silane having different chemical and/or physical characteristics. Each of these silanized sites would also be isolated from one another due to the unmodified inert PTFE material surrounding each site. The modified material would then be useful in fabricating the bioprobe.

EXAMPLE

A 10×20 cm² piece of expanded (e)PTFE (Goretex membrane material) and PTFE (smooth solid sheet) were exposed for 30 minutes to a $H_2$/methanol RFGD plasma, and subsequently dipped in and out; dipped for 1 minute; dipped for 10 minutes; dipped for 30 minutes; refluxed for 15 minutes and then refluxed for 4 hours in a one percent aminopropyltrietoxysilane (APTES) in a 99% hexane solution. Electron spectroscopy for chemical analysis (ESCA) results are listed in Table III below:

TABLE III

ESCA ATOMIC RATIOS
(APTES refunctionalized Oxy-Fluoro materials)

| Sample | C/F | C/O | Si/F | Si/N |
|---|---|---|---|---|
| Unmodified ePTFE | 0.43 | — | — | — |
| 30 min. $H_2$/MeOH RFGD oxy-fluoro ePTFE | 0.93 | 15.0 | — | — |
| Quick dip of oxy-fluoro ePTFE in APTES | 1.22 | 4.1 | 0.17 | 0.95 |
| 1 minute dip | 1.53 | 4.0 | 0.21 | 0.98 |
| 10 min. dip | 1.51 | 3.1 | 0.27 | 0.99 |
| 30 min. dip | 2.4 | 2.6 | 0.54 | 1.05 |
| 15 min. reflux of oxy-fluoro ePTFE in APTES | 9.4 | 2.1 | 2.93 | 0.97 |
| 4 hour reflux | — | 2.1 | — | 1.03 |
| Unmodified PTFE | 0.48 | — | — | — |
| 30 min. $H_2$/MeOH RFGD oxy-fluoro PTFE | 1.5 | 8.7 | — | — |
| Quick dip in APTES | 1.8 | 3.3 | 0.23 | 0.97 |
| 10 minute dip | 2.86 | 3.1 | 0.44 | 0.93 |
| 30 minute dip | 2.24 | 3.1 | 0.40 | 0.99 |

The data in Table III indicate a polymer surface comprising both silane and fluorine functionality with increasing silane (observed through increases in the Si/F ratios) as a function of dip time in the APTES/hexane solutions.

Exposure to the APTES/hexane solutions under refluxing conditions allowed for the formation of a thick overcoating of APTES such that no signal from the underlying ePTFE was observed, i.e. total coverage of the ePTFE is facilitated. The Si/N atomic ratios as provided in Table III show the retention of the organosilicon molecular unit in that the corrected ratio is calculated to be within error limits 1.00, i.e. the expected atomic ratio for APTES. On all samples vigorous washing in a variety of polar and nonpolar solvents (including hexane, methanol, chloroform and THF) were performed immediately following refunctionalization and up to six months later with no detection of change in the refunctionalized surfaces, illustrating the permanency and stability of the refunctionalized oxy-fluoro materials. Further, in all cases a piece of the unmodified original ePTFE material was treated identically as a control and no detection of silanization or addition of oxygen was observed, i.e. ESCA results gave atomic ratios identical to those normally found for unmodified PTFE or ePTFE materials with no detection of silicon or oxygen.

All of the modified/refunctionalized materials (except those refluxed for the 4 hour period) showed an extremely high hydrophobic character, i.e. contact angles of polar liquids including water, formamide and glycerol were all >110° (see Table IV below). The materials refluxed for 15 minutes and for 4 hours (which from ESCA results showed total coverage) were observed to have increased wettability characteristics tending towards but not completely approaching those associated with pure APTES films.

TABLE IV

WETTABILITY DATA

| Liquid | Suface Tension dynes/cm | Contact angle θ as measured on each sample | | | | |
|---|---|---|---|---|---|---|
| | | 1 | 2 | 3 | 4 | 5 |
| Water | 72.4 | 148 | 117 | 66 | 110 | 90 |
| Glycerol | 64.8 | 151 | 100 | 63 | 126 | 85 |
| Formamide | 58.9 | 123 | 112 | 40 | 115 | 80 |
| Thiodiglycol | 53.5 | 133 | 112 | 35 | 35 | 85 |
| Methylene Iodide | 49.0 | 128 | 81 | 38 | 33 | 40 |
| S-Tetrabromoethane | 49.8 | 125 | 76 | — | — | — |
| 1-Bromonaphthalene | 45.0 | 114 | 0 | 25 | 40 | 10 |
| o-Dibromo-benzene | 43.3 | 118 | 0 | — | — | — |
| Propylene Carbonate | 41.8 | 119 | 0 | — | — | — |
| 1-Methyl naphthalene | 39.3 | 97 | 0 | 15 | 45 | 0 |
| Dimethyl-formamide | 37.5 | 113 | 0 | — | 0 | 0 |
| Dicyclohexyl | 32.7 | 66 | 0 | 6 | 0 | 0 |
| n-Hexadecane | 27.6 | 35 | 0 | 0 | 0 | 0 |
| n-Tridecane | 26.0 | 0 | 0 | 0 | 0 | 0 |

1 - unmodified ePTFE
2 - 30 minute $H_2$/MeOH RFGD oxy-fluoro PTFE membrane
3 - APTES Film
4 - Oxy-fluoro membrane dipped in 1% APTES/99% Hexane for 15 minutes
5 - Oxy-fluoro membrane refluxed for 15 minutes in APTES solution

EXAMPLE IX

A study similar to that described in Example VIII was conducted, but instead of employing the silane APTES, a 3-mercaptopropyltrimetoxysilane (MPTMS) was utilized. Without using a solid, smooth PTFE, an original sample of expanded (e)PTFE material (Goretex) was modified by forming an oxyfluorinated material according to the foregoing examples using a 20 minute $H_2$/water RFGD treatment. The results identified by ESCA are provided in Table V below. Similar to the results listed for Example VIII, the data shows increased amounts of MPTMS with an increase in exposure time, however, an ever present amount of fluorine surface functionality resulted in a very hydrophobic refunctionalized surface.

TABLE V

ESCA ATOMIC RATIOS
(MPTMS refunctionalized oxy-fluoro materials)

| Sample | C/F | C/O | Si/F | Si/S |
|---|---|---|---|---|
| Unmodified ePTFE | 0.43 | — | — | — |
| 20 min. $H_2/H_2O$ RFGD oxy-fluoro ePTFE | 0.65 | 16.0 | — | — |
| quick dip of oxy-fluoro ePTFE in APTES | 0.77 | 12.3 | 0.06 | 1.03 |
| 1 minute dip | 0.73 | 11.0 | 0.08 | 1.00 |
| 5 minute dip | 0.80 | 11.6 | 0.07 | 1.05 |

EXAMPLE X

A similar study to that of Example VIII was performed using glycidoxypropyltrimethoxysilane (GPTMS). The polymer employed was PTFE (Teflon ® tape) modified by a 30 minute treatment to a $H_2$/methanol vapor RFGD. The films were dipped for one minute in a one percent GPTMS/99% hexane solution and a one percent GPTMS/1% Acetic acid/98% hexane solution. This was done in order to determine the effect of pH change on reaction rate. It will be noted from the ESCA analysis that Si/F atomic ratios (Table VI below) that the extent of the reaction is greatly enhanced by increasing the acidity of the silane solution. This feature then predicts the use of the modified oxyfluoro materials as pH sensitive membrane materials, i.e. pH sensors.

TABLE VI

ESCA ATOMIC RATIOS
(GPTMS refunctionalized Oxy-Fluoro materials)

| Sample | C/F | C/O | Si/F |
|---|---|---|---|
| Unmodified ePTFE | 0.43 | — | — |
| 30 min. $H_2$/MeOH RFGD oxy-fluoro of ePTFE | 0.90 | 10.01 | — |
| Quick dip of oxy-fluoro ePTFE in a 1% GPTMS:99% Hexane solution | 1.11 | 4.2 | 0.07 |
| Quick dip of oxy-fluoro ePTFE in a 1% GPTMS:1% Acetic acid:98% Hexane solution | 11.1 | 1.71 | 1.68 |

EXAMPLE XI

Expanded PTFE and solid smooth films of PTFE were prepared as in Example VIII, i.e. the films coated with APTES from a quick dip; 1 minute dip; 15 minute dip and a 30 minute dip, were exposed for 24 hours to the fluorophore, fluorescein isothiocyanate (FITC), which at a pH of 10 reacts preferentially with amine functionality, i.e. the FITC was used to label the free amines of the APTES location on the APTES-oxyfluoropolymeric surface. The FITC fluorescent molecule and laser fluorescence data (see Table VII below) show the increase in bonded FITC as a function of increase in APTES.

TABLE VII

Surface Fluorescence Intensity (background subtracted) and Surface Concentration of FITC Reacted to APTES Amine Functionality On a Oxy-Fluoro/APTES ePTFE Membrane

| Sample | Fluorescence Intensity | Surface Concentration |
|---|---|---|
| Unmodified ePTFE | 0.00 | 0.00 |
| FITC reacted to oxy-fluoro ePTFE quick dipped in APTES | 1.22 | 2.89 nmol/cm$^2$ |
| FITC reacted to oxy-fluoro ePTFE dipped in APTES for 1 minute | 1.34 | 3.17 nmol/cm$^2$ |
| FITC reacted to oxy-fluoro ePTFE dipped in APTES for 5 minutes | 1.45 | 3.44 nmol/cm$^2$ |
| FITC reacted to oxy-fluoro ePTFE dipped in APTES for 15 minutes | 1.82 | 4.31 nmol/cm$^2$ |

EXAMPLE XII

At a pH of 10, FITC was observed by both ESCA (observed through the N/F and S/F ratios listed in Table VIII below) and laser fluorescence spectroscopy to react directly, i.e. without the APTES amine present to oxyfluoropolymer material modified by exposing expanded PTFE (Goretex) and Teflon (PTFE) tape for 30 minutes to RFGD and a plasma consisting of $H_2$/Methanol and 20 minutes to $H_2/H_2O$. This was an unusual result considering FITC'S normal reactivity limitation to basic amines. This provides evidence for the existence of a strong anionic oxygen (O$^-$) on the oxyfluoropolymer surface, and further suggests the reactivity to all atoms and/or molecules which show reactivity to strong O$^-$ sites.

TABLE VIII

ESCA ATOMIC RATIOS
(FITC reacted to oxy-fluoro ePTFE)

| Sample | C/F | C/O | N/F | S/F |
|---|---|---|---|---|
| Unmodified ePTFE | 0.43 | — | — | — |
| 30 min. $H_2$/MeOH RFGD oxy-fluoro ePTFE | 0.90 | 10.0 | — | — |
| Oxy-fluoro ePTFE placed in FITC solution pH = 10 for 24 hours | 1.40 | 3.60 | 0.05 | 0.05 |

EXAMPLE XIII

Further testing for the presence of a strong oxygen group on the oxyfluoro surfaces was performed by using an (e)PTFE starting material and modifying its surface with a 30 minute treatment to a radio frequency glow discharge mixture of hydrogen/ methanol, so as to create the oxyfluoropolymeric surface. This material was then ultrasonicated in concentrated sodium hydroxide for 30 seconds using one piece as modified and another modified piece first rinsed in methanol before transference to the sodium hyroxide solution. Due to extreme hydrophobicity previously indicated for oxyfluoropolymers, the sample which was not first wet with nonpolar methanol did not sink into the sodium hydroxide solution. This material was forcibly clamped into the sodium hyroxide solution during the 30 seconds ultrasonication. The material first wet with methanol had the ability to enter the sodium hydroxide solution, and thus, did not need clamping. ESCA results listed in Table IX below indicate the ionic exchange which occurred between the oxyfluoropolymer and the sodium hydroxide solution. That is, the formation of a Na-O-ePTFE which from ESCA results occurs to a much greater extent on the material first wet with methanol. Only superficial sodium-O-bonding is noted on the material which required clamping into the sodium hydroxide solution. These results indicate the oxyfluoro materials and subsequently refunctionalized oxyfluoropolymers as ion exchange solid supports or membranes, particularly in the case of expanded PTFE (Goretex). Furthermore, due to the extreme hydrophobic nature of these materials as observed from the oxyfluoro material not first wet in methanol, the membranes would be useful as battery separator/membranes in cases where ion exchange without water or aqueous flow through a membrane is required. For example, high energy density batteries using lithium based electrodes are limited largely due to the need for a membrane which requires ion exchange from the lithium to an aqueous electrolyte without aqueous electrolyte coming in contact with the lithium metal.

TABLE IX

ESCA ATOMIC RATIOS
(NaOH reacted to oxy-fluoro ePTFE)

| Sample | C/F | C/O | Na/F |
|---|---|---|---|
| Unmodified ePTFE | 0.43 | — | — |
| 30 Min. H$_2$/MeOH RFGD oxy-fluoro ePTFE | 0.88 | 14.2 | — |
| Oxy-fluoro ePTFE ultrasonicated in concentrated NaOH for 30 seconds | 0.84 | 4.1 | 0.08 |
| Oxy-fluoro ePTFE ultrasonicated in concentrated NaOH for 30 seconds after pre-wetting in methanol | 2.7 | 2.5 | 0.57 |

The invention has been described in conjunction with specific examples thereof. This is illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

What is claimed is:

1. A refunctionalized oxyfluoropolymer comprising a fluoropolymer in which up to 98 percent of the surface fluorine atoms to depths from about 10 to about 100 Å have been permanently substituted with hydrogen and oxygen or oxygen-containing groups to form an oxyfluoropolymer of which from about 3 to about 30 percent of the substituted fluorine has been replaced with oxygen or oxygen-containing groups and from about 70 to about 97 percent of the fluorine has been replaced with hydrogen atoms, said oxyfluoropolymer being refunctionalized where from about 3 to about 100 percent of said oxygen or oxygen-containing groups have covalently bonded thereto a member selected from the group consisting of an organosilane, alkali metal and isothiocyanate-containing fluorescent compound.

2. The refunctionalized oxyfluoropolymer of claim 1 wherein said oxygen or oxygen-containing groups have an organosilane group covalently bonded thereto.

3. The refunctionalized oxyfluoropolymer of claim 1 wherein said oxygen or oxygen-containing groups have an alkali metal covalently bonded thereto.

4. The refunctionalized oxyfluoropolymer of claim 1 wherein said oxygen or oxygen-containing groups have a isothiocyanate-containing fluorescent compound covalently bonded thereto.

5. The refunctionalized oxyfluoropolymer of claim 2 wherein the organosilane moiety covalently bonded to the oxygen or oxygen containing groups is of the formula:

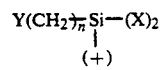

in which Y is a member selected from the group consisting of allyl, alkyl, haloalkyl, amino, mercapto, epoxy, glycidoxy, methacrylate, cyano and —CH$_2$CO$_2$alkyl and n is from 0 to 17 and X is independently selected from hydrogen, halogen, alkyl, haloalkyl, alkylamino, alkoxy and trialkylsiloxy.

6. The refunctionalized oxyfluoropolymer of claim 5 wherein n is 3 and Y is alkylamino, dialkylamino, mercapto or glycidoxy, X is chlorine, bromine, fluorine, alkyl having 1 to 4 carbon atoms, chloromethyl, monoethylamino, dimethylamino, methoxy, ethoxy, propoxy, butoxy or trimethylsiloxy.

7. The refunctionalized oxyfluoropolymer of claim 4 wherein the isothiocyanate-containing fluorescent compound is fluoresceinisothiocyanate.

8. The refunctionalized oxyfluoropolymer of claim 1 wherein the alkali metal is a member selected from the group consisting of sodium, potassium and lithium.

9. The refunctionalized oxyfluoropolymer of claim 2 wherein the fluoropolymer is PTFE or an expanded PTFE.

10. The refunctionalized oxyfluoropolymer of claim 3 wherein the fluoropolymer is PTFE or an expanded PTFE.

11. The refunctionalized oxyfluoropolymer of claim 4 wherein the fluoropolymer is PTFE or an expanded PTFE.

12. A biosensor comprising the organosilane refunctionalized oxyfluoropolymer of claim 2.

13. A battery separator comprising the alkali metal refunctionalized oxyfluoropolymer of claim 3.

14. An antibody based sensor comprising the isothiocyanate-containing fluorescent compound refunctionalized oxyfluoropolymer of claim 4.

15. An inert, non-fouling substrate comprising the refunctionalized oxyfluoropolymer of claim 1.

16. The inert, non-fouling substrate of claim 15 which is a membrane or filter.

17. The inert, non-fouling substrate of claim 15 which is a piezo and pyroelectric poled PVDF.

* * * * *